(12) United States Patent
Svendsen

(10) Patent No.: US 7,371,546 B2
(45) Date of Patent: May 13, 2008

(54) GLUCOAMYLASE VARIANTS

(75) Inventor: Allan Svendsen, Horsholm (DK)

(73) Assignee: Novozymes A/S, Bagsvaerd (DK)

( * ) Notice: Subject to any disclaimer, the term of this patent is extended or adjusted under 35 U.S.C. 154(b) by 141 days.

(21) Appl. No.: 10/491,046

(22) PCT Filed: Sep. 27, 2002

(86) PCT No.: PCT/DK02/00639

§ 371 (c)(1),
(2), (4) Date: Oct. 14, 2004

(87) PCT Pub. No.: WO03/029449

PCT Pub. Date: Apr. 10, 2003

(65) Prior Publication Data

US 2005/0048636 A1 Mar. 3, 2005

Related U.S. Application Data

(60) Provisional application No. 60/328,611, filed on Oct. 11, 2001.

(30) Foreign Application Priority Data

Oct. 1, 2001 (DK) .......................... PA 2001-01432

(51) Int. Cl.
*C12P 19/20* (2006.01)
*C12P 23/00* (2006.01)
*C12N 1/20* (2006.01)
*C12N 15/00* (2006.01)
*C12N 9/34* (2006.01)
*C11D 3/00* (2006.01)
*C07H 21/04* (2006.01)

(52) U.S. Cl. ................... 435/96; 435/254.3; 435/320.1; 435/69.1; 435/254.11; 435/205; 435/252.3; 510/320; 536/23.2

(58) Field of Classification Search ...................... None
See application file for complete search history.

(56) References Cited

U.S. PATENT DOCUMENTS 6,329,186 B1 * 12/2001 Nielsen et al. .............. 435/205

FOREIGN PATENT DOCUMENTS

| WO | WO 84/02921 | * | 8/1984 |
|---|---|---|---|
| WO | WO 92/00381 | | 1/1992 |
| WO | WO 98/03639 | | 1/1998 |
| WO | WO 00/04136 | | 1/2000 |
| WO | WO0004136 A1 | * | 1/2000 |
| WO | WO 00/34452 | | 6/2000 |
| WO | WO 01/04273 | | 1/2001 |

OTHER PUBLICATIONS

Hayashida et al., Molecular cloning of the glucoamylase I gene of *Aspergillus awamori* var. kwa. Agric. Biol. Chem. 1989, vol. 53: 923-829.*
Shibuya et al., Molecular cloning of the glucoamylase gene of *Aspergillus shirousami* and its ... Agric. Biol. Chem., 1990, vol. 54: 1905-1914.*
Hata Y et al., The glucoamylase cDNA from *Aspergillus oryzae*: its cloning ... Agric. Biol. Chem., 1991, vol. 55: 941-949.*
Cameron ER., Recent advances in transgenic technology, 1997, vol. 7: 253-265.*
Whisstock et al., Prediction of protein function from protein sequence and structure. Q. Reviews Biopys., 2003, pp. 307-340.*
Ford C., Improving operating performance of glucoamylase by mutagenesis. Current Opininon in Biotechnol., 1999, vol. 10: 353-357.*
Fang et al., Protein engineering of *Aspergillus awamori* glucoamylase to increase its pH optimum. Prot. Eng., 1998, vol. 11(5): 383-388.*
Chen et al., Protein Engineering, vol. 9, pp. 499-505, (1996).
Chen et al., Protein Engineering, vol. 8, pp. 575-582, (1995).
Chen et al., Biochem. J., vol. 301, pp. 275-281, (1994).
Fierobe et al., Biochemistry, vol. 35, pp. 8696-8704, (1996).
Li et al., Protein Engineering, vol. 10, pp. 1199-1204, (1997).
Ford et al., "Mutagenesis of *Aspergillus awamori* Glucoamylase to Improve Thermal Stability and Substrate Specificity", Program "Enzyme Engineering XIV" Oct. 12-17, 1997, Holiday Inn Lido Beijing, China.
Berland et al., Biochemistry, vol. 34, pp. 10153-10161, (1995).
Ballery et al., Protein Engineering, vol. 3, No. 3, pp. 199-204, (1990).
Sierks et al., Protein Engineering, vol. 3, No. 3, pp. 193-198, (1990).
Harris et al., Biochemistry, vol. 32, pp. 1618-1626, (1993).
Aleshin et al., The Journal of Biological Chemistry, vol. 267, No. 27, pp. 19291-19298, (1992).
Svensson et al., Eur. J. Biochem, vol. 154, pp. 497-502, (1986).
Svensson et al., Carlsberg Res. Commun., vol. 48, p. 529-544, (1983).
Aleshin et al., Biochemistry, vol. 35, pp. 8319-8328, (1996).
Frandsen et al., Biochemistry, vol. 34, pp. 10162-10169, (1995).
Sierks et al., Protein Engineering, vol. 2, No. 8, pp. 621-625, (1989).

* cited by examiner

*Primary Examiner*—Rebecca E. Prouty
*Assistant Examiner*—Ganapathirama Raghu
(74) *Attorney, Agent, or Firm*—Michael W. Krenicky

(57) ABSTRACT

The invention relates to a variant of a parental fungal glucoamylase, which exhibits improved thermal stability and/or increased specific activity using saccharide substrates.

16 Claims, No Drawings

SEQUENCE LISTING

```
<160> NUMBER OF SEQ ID NOS: 5

<210> SEQ ID NO 1
<211> LENGTH: 1605
<212> TYPE: DNA
<213> ORGANISM: Aspergillus niger
<220> FEATURE:
<221> NAME/KEY: sig_peptide
<222> LOCATION: (1)..(72)
<220> FEATURE:
<221> NAME/KEY: CDS
<222> LOCATION: (1)..(1602)
<220> FEATURE:
<221> NAME/KEY: mat_peptide
<222> LOCATION: (73)..(1602)

<400> SEQUENCE: 1 atg tcg ttc cga tct cta ctc gcc ctg agc ggc ctc gtc tgc aca ggg      48
Met Ser Phe Arg Ser Leu Leu Ala Leu Ser Gly Leu Val Cys Thr Gly
            -20                 -15                 -10 ttg gca aat gtg att tcc aag cgc gcg acc ttg gat tca tgg ttg agc      96
Leu Ala Asn Val Ile Ser Lys Arg Ala Thr Leu Asp Ser Trp Leu Ser
         -5                  -1   1                   5 aac gaa gcg acc gtg gct cgt act gcc atc ctg aat aac atc ggg gcg     144
Asn Glu Ala Thr Val Ala Arg Thr Ala Ile Leu Asn Asn Ile Gly Ala
             10                  15                  20 gac ggt gct tgg gtg tcg ggc gcg gac tct ggc att gtc gtt gct agt     192
Asp Gly Ala Trp Val Ser Gly Ala Asp Ser Gly Ile Val Val Ala Ser
 25                  30                  35                  40 ccc agc acg gat aac ccg gac tac ttc tac acc tgg act cgc gac tct     240
Pro Ser Thr Asp Asn Pro Asp Tyr Phe Tyr Thr Trp Thr Arg Asp Ser
                     45                  50                  55 ggt ctc gtc ctc aag acc ctc gtc gat ctc ttc cga aat gga gat acc     288
Gly Leu Val Leu Lys Thr Leu Val Asp Leu Phe Arg Asn Gly Asp Thr
                 60                  65                  70 agt ctc ctc tcc acc att gag aac tac atc tcc gcc cag gca att gtc     336
Ser Leu Leu Ser Thr Ile Glu Asn Tyr Ile Ser Ala Gln Ala Ile Val
             75                  80                  85
```

|  |  |
|---|---:|
| cag ggt atc agt aac ccc tct ggt gat ctg tcc agc ggc gct ggt ctc<br>Gln Gly Ile Ser Asn Pro Ser Gly Asp Leu Ser Ser Gly Ala Gly Leu<br>      90                         95                    100 | 384 |
| ggt gaa ccc aag ttc aat gtc gat gag act gcc tac act ggt tct tgg<br>Gly Glu Pro Lys Phe Asn Val Asp Glu Thr Ala Tyr Thr Gly Ser Trp<br>105                     110                    115                    120 | 432 |
| gga cgg ccg cag cga gat ggt ccg gct ctg aga gca act gct atg atc<br>Gly Arg Pro Gln Arg Asp Gly Pro Ala Leu Arg Ala Thr Ala Met Ile<br>                    125                    130                    135 | 480 |
| ggc ttc ggg cag tgg ctg ctt gac aat ggc tac acc agc acc gca acg<br>Gly Phe Gly Gln Trp Leu Leu Asp Asn Gly Tyr Thr Ser Thr Ala Thr<br>          140                    145                    150 | 528 |
| gac att gtt tgg ccc ctc gtt agg aac gac ctg tcg tat gtg gct caa<br>Asp Ile Val Trp Pro Leu Val Arg Asn Asp Leu Ser Tyr Val Ala Gln<br>               155                    160                    165 | 576 |
| tac tgg aac cag aca gga tat gat ctc tgg gaa gaa gtc aat ggc tcg<br>Tyr Trp Asn Gln Thr Gly Tyr Asp Leu Trp Glu Glu Val Asn Gly Ser<br>          170                    175                    180 | 624 |
| tct ttc ttt acg att gct gtg caa cac cgc gcc ctt gtc gaa ggt agt<br>Ser Phe Phe Thr Ile Ala Val Gln His Arg Ala Leu Val Glu Gly Ser<br>185                     190                    195                    200 | 672 |
| gcc ttc gcg acg gcc gtc ggc tcg tcc tgc tcc tgg tgt gat tct cag<br>Ala Phe Ala Thr Ala Val Gly Ser Ser Cys Ser Trp Cys Asp Ser Gln<br>                    205                    210                    215 | 720 |
| gca ccc gaa att ctc tgc tac ctg cag tcc ttc tgg acc ggc agc ttc<br>Ala Pro Glu Ile Leu Cys Tyr Leu Gln Ser Phe Trp Thr Gly Ser Phe<br>               220                    225                    230 | 768 |
| att ctg gcc aac ttc gat agc agc cgt tcc ggc aag gac gca aac acc<br>Ile Leu Ala Asn Phe Asp Ser Ser Arg Ser Gly Lys Asp Ala Asn Thr<br>          235                    240                    245 | 816 |
| ctc ctg gga agc atc cac acc ttt gat cct gag gcc gca tgc gac gac<br>Leu Leu Gly Ser Ile His Thr Phe Asp Pro Glu Ala Ala Cys Asp Asp<br>          250                    255                    260 | 864 |
| tcc acc ttc cag ccc tgc tcc ccg cgc gcg ctc gcc aac cac aag gag<br>Ser Thr Phe Gln Pro Cys Ser Pro Arg Ala Leu Ala Asn His Lys Glu<br>265                   270                    275                    280 | 912 |
| gtt gta gac tct ttc cgc tca atc tat acc ctc aac gat ggt ctc agt<br>Val Val Asp Ser Phe Arg Ser Ile Tyr Thr Leu Asn Asp Gly Leu Ser<br>                    285                    290                    295 | 960 |
| gac agc gag gct gtt gcg gtg ggt cgg tac cct gag gac acg tac tac<br>Asp Ser Glu Ala Val Ala Val Gly Arg Tyr Pro Glu Asp Thr Tyr Tyr<br>                  300                    305                    310 | 1008 |
| aac ggc aac ccg tgg ttc ctg tgc acc ttg gct gcc gca gag cag ttg<br>Asn Gly Asn Pro Trp Phe Leu Cys Thr Leu Ala Ala Ala Glu Gln Leu<br>               315                    320                    325 | 1056 |
| tac gat gct cta tac cag tgg gac aag cag ggg tcg ttg gag gtc aca<br>Tyr Asp Ala Leu Tyr Gln Trp Asp Lys Gln Gly Ser Leu Glu Val Thr<br>          330                    335                    340 | 1104 |
| gat gtg tcg ctg gac ttc ttc aag gca ctg tac agc gat gct gct act<br>Asp Val Ser Leu Asp Phe Phe Lys Ala Leu Tyr Ser Asp Ala Ala Thr<br>345                   350                    355                    360 | 1152 |
| ggc acc tac tct tcg tcc agt tcg act tat agt agc att gta gat gcc<br>Gly Thr Tyr Ser Ser Ser Ser Ser Thr Tyr Ser Ser Ile Val Asp Ala<br>                    365                    370                    375 | 1200 |
| gtg aag act ttc gcc gat ggc ttc gtc tct att gtg gaa act cac gcc<br>Val Lys Thr Phe Ala Asp Gly Phe Val Ser Ile Val Glu Thr His Ala<br>               380                    385                    390 | 1248 |
| gca agc aac ggc tcc atg tcc gag caa tac gac aag tct gat ggc gag<br>Ala Ser Asn Gly Ser Met Ser Glu Gln Tyr Asp Lys Ser Asp Gly Glu | 1296 |

-continued

```
                      395                     400                       405
cag ctt tcc gct cgc gac ctg acc tgg tct tat gct gct ctg ctg acc        1344
Gln Leu Ser Ala Arg Asp Leu Thr Trp Ser Tyr Ala Ala Leu Leu Thr
410                 415                 420 gcc aac aac cgt cgt aac tcc gtc gtg cct gct tct tgg ggc gag acc        1392
Ala Asn Asn Arg Arg Asn Ser Val Val Pro Ala Ser Trp Gly Glu Thr
425                 430                 435                 440 tct gcc agc agc gtg ccc ggc acc tgt gcg gcc aca tct gcc att ggt        1440
Ser Ala Ser Ser Val Pro Gly Thr Cys Ala Ala Thr Ser Ala Ile Gly
                445                 450                 455 acc tac agc agt gtg act gtc acc tcg tgg ccg agt atc gtg gct act        1488
Thr Tyr Ser Ser Val Thr Val Thr Ser Trp Pro Ser Ile Val Ala Thr
            460                 465                 470 ggc ggc acc act acg acg gct acc ccc act gga tcc ggc agc gtg acc        1536
Gly Gly Thr Thr Thr Thr Ala Thr Pro Thr Gly Ser Gly Ser Val Thr
        475                 480                 485 tcg acc agc aag acc acc gcg act gct agc aag acc agc acc acg acc        1584
Ser Thr Ser Lys Thr Thr Ala Thr Ala Ser Lys Thr Ser Thr Thr Thr
    490                 495                 500 cgc tct ggt atg tca ctg tga                                            1605
Arg Ser Gly Met Ser Leu
505                 510

<210> SEQ ID NO 2
<211> LENGTH: 534
<212> TYPE: PRT
<213> ORGANISM: Aspergillus niger

<400> SEQUENCE: 2

Met Ser Phe Arg Ser Leu Leu Ala Leu Ser Gly Leu Val Cys Thr Gly
                -20                 -15                 -10

Leu Ala Asn Val Ile Ser Lys Arg Ala Thr Leu Asp Ser Trp Leu Ser
            -5                  -1  1               5

Asn Glu Ala Thr Val Ala Arg Thr Ala Ile Leu Asn Ile Gly Ala
        10                  15                  20

Asp Gly Ala Trp Val Ser Gly Ala Asp Ser Gly Ile Val Val Ala Ser
25                  30                  35                  40

Pro Ser Thr Asp Asn Pro Asp Tyr Phe Tyr Thr Trp Thr Arg Asp Ser
                45                  50                  55

Gly Leu Val Leu Lys Thr Leu Val Asp Leu Phe Arg Asn Gly Asp Thr
            60                  65                  70

Ser Leu Leu Ser Thr Ile Glu Asn Tyr Ile Ser Ala Gln Ala Ile Val
        75                  80                  85

Gln Gly Ile Ser Asn Pro Ser Gly Asp Leu Ser Ser Gly Ala Gly Leu
    90                  95                  100

Gly Glu Pro Lys Phe Asn Val Asp Glu Thr Ala Tyr Thr Gly Ser Trp
105                 110                 115                 120

Gly Arg Pro Gln Arg Asp Gly Pro Ala Leu Arg Ala Thr Ala Met Ile
                125                 130                 135

Gly Phe Gly Gln Trp Leu Leu Asp Asn Gly Tyr Thr Ser Thr Ala Thr
            140                 145                 150

Asp Ile Val Trp Pro Leu Val Arg Asn Asp Leu Ser Tyr Val Ala Gln
        155                 160                 165

Tyr Trp Asn Gln Thr Gly Tyr Asp Leu Trp Glu Glu Val Asn Gly Ser
    170                 175                 180

Ser Phe Phe Thr Ile Ala Val Gln His Arg Ala Leu Val Glu Gly Ser
185                 190                 195                 200
```

```
Ala Phe Ala Thr Ala Val Gly Ser Ser Cys Ser Trp Cys Asp Ser Gln
            205                 210                 215

Ala Pro Glu Ile Leu Cys Tyr Leu Gln Ser Phe Trp Thr Gly Ser Phe
            220                 225                 230

Ile Leu Ala Asn Phe Asp Ser Ser Arg Ser Gly Lys Asp Ala Asn Thr
            235                 240                 245

Leu Leu Gly Ser Ile His Thr Phe Asp Pro Glu Ala Ala Cys Asp Asp
            250                 255                 260

Ser Thr Phe Gln Pro Cys Ser Pro Arg Ala Leu Ala Asn His Lys Glu
265                 270                 275                 280

Val Val Asp Ser Phe Arg Ser Ile Tyr Thr Leu Asn Asp Gly Leu Ser
                285                 290                 295

Asp Ser Glu Ala Val Ala Val Gly Arg Tyr Pro Glu Asp Thr Tyr Tyr
                300                 305                 310

Asn Gly Asn Pro Trp Phe Leu Cys Thr Leu Ala Ala Glu Gln Leu
            315                 320                 325

Tyr Asp Ala Leu Tyr Gln Trp Asp Lys Gln Gly Ser Leu Glu Val Thr
            330                 335                 340

Asp Val Ser Leu Asp Phe Phe Lys Ala Leu Tyr Ser Asp Ala Ala Thr
345                 350                 355                 360

Gly Thr Tyr Ser Ser Ser Ser Thr Tyr Ser Ser Ile Val Asp Ala
                365                 370                 375

Val Lys Thr Phe Ala Asp Gly Phe Val Ser Ile Val Glu Thr His Ala
                380                 385                 390

Ala Ser Asn Gly Ser Met Ser Glu Gln Tyr Asp Lys Ser Asp Gly Glu
            395                 400                 405

Gln Leu Ser Ala Arg Asp Leu Thr Trp Ser Tyr Ala Ala Leu Leu Thr
            410                 415                 420

Ala Asn Asn Arg Arg Asn Ser Val Val Pro Ala Ser Trp Gly Glu Thr
425                 430                 435                 440

Ser Ala Ser Ser Val Pro Gly Thr Cys Ala Ala Thr Ser Ala Ile Gly
                445                 450                 455

Thr Tyr Ser Ser Val Thr Val Thr Ser Trp Pro Ser Ile Val Ala Thr
            460                 465                 470

Gly Gly Thr Thr Thr Thr Ala Thr Pro Thr Gly Ser Gly Ser Val Thr
            475                 480                 485

Ser Thr Ser Lys Thr Thr Ala Thr Ala Ser Lys Thr Ser Thr Thr Thr
            490                 495                 500

Arg Ser Gly Met Ser Leu
505                 510

<210> SEQ ID NO 3
<211> LENGTH: 68
<212> TYPE: DNA
<213> ORGANISM: Artificial Sequence
<220> FEATURE:
<223> OTHER INFORMATION: Primer

<400> SEQUENCE: 3
ggggatcatg ataggactag ccatattaat gaagggcata taccacgcct tggacctgcg    60
ttatagcc                                                              68

<210> SEQ ID NO 4
<211> LENGTH: 25
<212> TYPE: DNA
```

```
<213> ORGANISM: Artificial Sequence
<220> FEATURE:
<223> OTHER INFORMATION: Primer

<400> SEQUENCE: 4
gcaacgaagc gcccgtggct cgtac                                        25

<210> SEQ ID NO 5
<211> LENGTH: 640
<212> TYPE: PRT
<213> ORGANISM: Aspergillus niger

<400> SEQUENCE: 5
```

| Met | Ser | Phe | Arg | Ser | Leu | Leu | Ala | Leu | Ser | Gly | Leu | Val | Cys | Thr | Gly |
|---|---|---|---|---|---|---|---|---|---|---|---|---|---|---|---|
| 1 | | | | 5 | | | | | 10 | | | | | 15 | |

| Leu | Ala | Asn | Val | Ile | Ser | Lys | Arg | Ala | Thr | Leu | Asp | Ser | Trp | Leu | Ser |
|---|---|---|---|---|---|---|---|---|---|---|---|---|---|---|---|
| | | | 20 | | | | | 25 | | | | | 30 | | |

| Asn | Glu | Ala | Thr | Val | Ala | Arg | Thr | Ala | Ile | Leu | Asn | Asn | Ile | Gly | Ala |
| | | 35 | | | | | 40 | | | | | 45 | | | |

| Asp | Gly | Ala | Trp | Val | Ser | Gly | Ala | Asp | Ser | Gly | Ile | Val | Val | Ala | Ser |
| 50 | | | | | 55 | | | | | 60 | | | | | |

| Pro | Ser | Thr | Asp | Asn | Pro | Asp | Tyr | Phe | Tyr | Thr | Trp | Thr | Arg | Asp | Ser |
| 65 | | | | 70 | | | | | 75 | | | | | 80 | |

| Gly | Leu | Val | Leu | Lys | Thr | Leu | Val | Asp | Leu | Phe | Arg | Asn | Gly | Asp | Thr |
| | | | | 85 | | | | | 90 | | | | | 95 | |

| Ser | Leu | Leu | Ser | Thr | Ile | Glu | Asn | Tyr | Ile | Ser | Ala | Gln | Ala | Ile | Val |
| | | | 100 | | | | | 105 | | | | | 110 | | |

| Gln | Gly | Ile | Ser | Asn | Pro | Ser | Gly | Asp | Leu | Ser | Ser | Gly | Ala | Gly | Leu |
| | | 115 | | | | | 120 | | | | | 125 | | | |

| Gly | Glu | Pro | Lys | Phe | Asn | Val | Asp | Glu | Thr | Ala | Tyr | Thr | Gly | Ser | Trp |
| | | 130 | | | | | 135 | | | | | 140 | | | |

| Gly | Arg | Pro | Gln | Arg | Asp | Gly | Pro | Ala | Leu | Arg | Ala | Thr | Ala | Met | Ile |
| 145 | | | | | 150 | | | | | 155 | | | | | 160 |

| Gly | Phe | Gly | Gln | Trp | Leu | Leu | Asp | Asn | Gly | Tyr | Thr | Ser | Thr | Ala | Thr |
| | | | | 165 | | | | | 170 | | | | | 175 | |

| Asp | Ile | Val | Trp | Pro | Leu | Val | Arg | Asn | Asp | Leu | Ser | Tyr | Val | Ala | Gln |
| | | | 180 | | | | | 185 | | | | | 190 | | |

| Tyr | Trp | Asn | Gln | Thr | Gly | Tyr | Asp | Leu | Trp | Glu | Glu | Val | Asn | Gly | Ser |
| | | | 195 | | | | | 200 | | | | | 205 | | |

| Ser | Phe | Phe | Thr | Ile | Ala | Val | Gln | His | Arg | Ala | Leu | Val | Glu | Gly | Ser |
| | | 210 | | | | | 215 | | | | | 220 | | | |

| Ala | Phe | Ala | Thr | Ala | Val | Gly | Ser | Ser | Cys | Ser | Trp | Cys | Asp | Ser | Gln |
| 225 | | | | | 230 | | | | | 235 | | | | | 240 |

| Ala | Pro | Glu | Ile | Leu | Cys | Tyr | Leu | Gln | Ser | Phe | Trp | Thr | Gly | Ser | Phe |
| | | | | 245 | | | | | 250 | | | | | 255 | |

| Ile | Leu | Ala | Asn | Phe | Asp | Ser | Ser | Arg | Ser | Gly | Lys | Asp | Ala | Asn | Thr |
| | | | 260 | | | | | 265 | | | | | 270 | | |

| Leu | Leu | Gly | Ser | Ile | His | Thr | Phe | Asp | Pro | Glu | Ala | Ala | Cys | Asp | Asp |
| | | | 275 | | | | | 280 | | | | | 285 | | |

| Ser | Thr | Phe | Gln | Pro | Cys | Ser | Pro | Arg | Ala | Leu | Ala | Asn | His | Lys | Glu |
| | | 290 | | | | | 295 | | | | | 300 | | | |

| Val | Val | Asp | Ser | Phe | Arg | Ser | Ile | Tyr | Thr | Leu | Asn | Asp | Gly | Leu | Ser |
| 305 | | | | | 310 | | | | | 315 | | | | | 320 |

| Asp | Ser | Glu | Ala | Val | Ala | Val | Gly | Arg | Tyr | Pro | Glu | Asp | Thr | Tyr | Tyr |
| | | | | 325 | | | | | 330 | | | | | 335 | |

```
                                    -continued
Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
            435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
            515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640
```

GLUCOAMYLASE VARIANTS

CROSS-REFERENCE TO RELATED APPLICATIONS

This application is a 35 U.S.C. 371 national application of PCT/DK02/00639 filed 27 Sep.2002, which claims priority or the benefit under 35 U.S.C. 119 of Danish application no. PA 2001 01432, filed 1 Oct. 2001, and U.S. provisional application No. 60/328,611, filed 11 Oct. 2001, the contents of which are fully incorporated herein by reference.

FIELD OF THE INVENTION

The present invention relates to glucoamylase variants (mutants) of parent AMG, in particular with altered thermal stability and/or altered specific activity suitable for, e.g., starch conversion, e.g., for producing glucose from starch. More specifically, the present invention relates to glucoamylase enzyme variants and the use of such variant enzymes.

BACKGROUND OF THE INVENTION

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeasts, with those from *Aspergillus* being commercially most important.

Commercially, the glucoamylase enzyme is used to convert corn starch which is already partially hydrolyzed by an alpha-amylase to glucose. The glucose is further converted by glucose isomerase to a mixture composed almost equally of glucose and fructose. This mixture, or the mixture further enriched with fructose, is the commonly used high fructose corn syrup commercialized throughout the world. This syrup is the world's largest tonnage product produced by an enzymatic process. The three enzymes involved in the conversion of starch to fructose are among the most important industrial enzymes produced.

One of the main problems that exist with regard to the commercial use of glucoamylase in the production of high fructose corn syrup is the relatively low thermal stability of glucoamylase. Glucoamylase is not as thermally stable as alpha-amylase or glucose isomerase and it is most active and stable at lower pH's than either alpha-amylase or glucose isomerase. Accordingly, it must be used in a separate vessel at a lower temperature and pH.

Glucoamylase from *Aspergillus niger* has a catalytic (aa 1-440) and a starch binding domain (aa 509-616) separated by a long and highly O-glycosylated linker (Svensson et al. (1983), *Carsberg Res. Commun.* 48, 529-544, 1983 and (1986), *Eur. J. Biochem.* 154, 497-502). The catalytic domain (aa 1471) of glucoamylase from *A. awamori* var. X100 adopt an (alpha/alpha)$_6$-fold in which six conserved alpha→alpha loop segments connect the outer and inner barrels (Aleshin et al. (1992), *J. Biol. Chem.* 267, 19291-19298). Crystal structures of glucoamylase in complex with 1-deoxynojirimycin (Harris et al. (1993), *Biochemistry*, 32, 1618-1626) and the pseudotetrasaccharide inhibitors acarbose and D-glucodihydroacarbose (Aleshin et al. (1996), *Biochemistry* 35, 8319-8328) furthermore are compatible with glutamic 0.35 acids 179 and 400 acting as general acid and base, respectively. The crucial role of these residues during catalysis have also been studied using protein engineering (Sierks et al. (1990), *Protein Engng.* 3, 193-198; Frandsen et al. (1994), *Biochemistry*, 33, 13808-13816).

Glucoamylase-carbohydrate interactions at four glycosyl residue binding subsites, −1, +1, +2, and +3 are highlighted in glucoamylase-complex structures (Aleshin et al. (1996), *Biochemistry* 35, 8319-8328) and residues important for binding and catalysis have been extensively investigated using site-directed mutants coupled with kinetic analysis (Sierks et al. (1989), *Protein Engng.* 2, 621-625; Sierks et al. (1990), *Protein Engng.* 3, 193-198; Berland et al. (1995), *Biochemistry*, 34, 10153-10161; Frandsen et al. (1995), *Biochemistry*, 34, 10162-10169.

Different substitutions in *A. niger* glucoamylase to enhance the thermal stability have been described: i) substitution of alpha-helical glycines: G137A and G139A (Chen et al. (1996), *Prot. Engng.* 9, 499-505); ii) elimination of the fragile Asp-X peptide bonds, D257E and D293E/Q (Chen et al. (1995), *Prot. Engng.* 8, 575-582); prevention of deamidation in N182 (Chen et al. (1994), *Biochem. J.* 301, 275-281); iv) engineering of additional disulphide bond, A246C (Fierobe et al. (1996), *Biochemistry*, 35, 8698-8704; and v) introduction of Pro residues in position A435 and S436 (Li et al. (1997), *Protein Engng.* 10, 1199-1204. Furthermore Clark Ford presented a paper on Oct. 17, 1997, ENZYME ENGINEERING 14, Beijing/China October 12-17, 97, Abstract number: Abstract book p. 0-61. The abstract suggests mutations in positions G137A, N20C/A27C, and S30P in an (not disclosed) *Aspergillus awamori* glucoamylase to improve the thermal stability.

BRIEF DISCLOSURE OF THE INVENTION

The object of the present invention is to provide improved glucoamylase variants with altered properties, especially with altered thermostablility and/or altered specific activity suitable for use in, e.g., the saccharification step in starch conversion processes.

The term "a glucoamylase variant with altered thermostability" means in the context of the present invention a glucoamylase variant, which has a higher or lower $T_{1/2}$ (half-time) than the corresponding parent glucoamylase. The determination of T½ (Method I and Method II) is described in the "Materials & Methods" section of WO 00/04136.

The term "a glucoamylase variant with altered specific activity" means in the context of the present invention a glucoamylase variant with altered specific activity towards the alpha-1,4 linkages in the saccharide in question. The specific activity is determined as $k_{cat}$ or AGU/mg (measured as described in the "Materials & Methods" section of WO 00/04136). An increased specific activity means that the $k_{cat}$ or AGU/mg values are higher when compared to the $k_{cat}$ or AGU/mg values, respectively, of the corresponding parent glucoamylase.

The inventors of the present invention have provided a number of improved variants of a parent glucoamylase with altered thermostability and/or altered specific activity in comparison to the parent corresponding enzyme. The altered thermal stability is obtained by substituting selected positions in a parent glucoamylase. This will be described in details below.

Nomenclature

In the present description and claims, the conventional one-letter and three-letter codes for amino acid residues are used. For ease of reference, glucoamylase variants of the invention are described by use of the following nomenclature:

Original amino acid(s):position(s):substituted amino acid(s)

According to this nomenclature, for instance the substitution of alanine for asparagine in position 30 is shown as:

Ala30Asn or A30N a deletion of alanine in the same position is shown as:

Ala30* or A30* and insertion of an additional amino acid residue, such as lysine, is shown as:

Ala30AlaLys or A30AK

A deletion of a consecutive stretch of amino acid residues, such as amino acid residues 30-33, is indicated as (30-33)* or Δ(A30-N33).

Where a specific glucoamylase contains a "deletion" in comparison with other glucoamylases and an insertion is made in such a position this is indicated as:

*36Asp or *36D for insertion of an aspartic acid in the "deletion" position 36.

Multiple mutations are separated by plus signs, i.e.:

Ala30Asp+Glu34Ser or A30N+E34S representing mutations in positions 30 and 34 substituting alanine and glutamic acid for asparagine and serine, respectively. Multiple mutation may also be separated as follows, i.e., meaning the same as the plus sign:

Ala30Asp/Glu34Ser or A30N/E34S

When one or more alternative amino acid residues may be inserted in a given position it is indicated as A30N,E or A30N/E, or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, the latter substitution may also be indicated as:

A30R,N,D,A,C,Q,E,G,H,I,L,K,M,F,P,S,T,W,Y,V  or
A30X, where X denotes any other amino acid.

DETAILED DISCLOSURE OF THE INVENTION

A goal of the work underlying the present invention was to alter the thermal stability and/or alter the specific activity of particular glucoamylases which are obtainable from fungal organisms, in particular strains of the *Aspergillus* genus and which themselves had been selected on the basis of their suitable properties in starch conversion or alcohol fermentation.

Identifying Positions and/or Regions to be Mutated to Obtain Altered Thermostability and/or Altered Specific Activity Molecular dynamics (MD) simulations indicate the mobility of the amino acids in the protein structure (see McCammon, J A and Harvey, S C., (1987), "Dynamics of proteins and nucleic acids", Cambridge University Press). Such protein dynamics are often compared to the crystallographic B-factors (see Stout, G H and Jensen, L H, (1989), "X-ray structure determination", Wiley). By running the MD simulation at different protonation states of the titrate able residues, the pH related mobility of residues are simulated. Regions having the highest mobility or flexibility (here isotropic fluctuations) are selected for random mutagenesis. It is here understood that the high mobility found in certain areas of the protein, can be thermally improved by substituting residues in these residues. The substitutions are directed against residues that will change the dynamic behaviour of the residues to e.g. bigger side-chains and/or residues, which have capability of forming improved contacts to residues in the near environment. The AMG from *Aspergillus niger* was used for the MD simulation. How to carry out MD simulation is described in the Materials & Methods" section below.)

Regions found to be of interest for increasing the specific activity and/or improved thermostability are the regions in proximity to the active site. Regions positioned in between the α-helixes, and which may include positions on each side of the N- and C-terminal of the α-helixes, at the substrate-binding site is of importance for the activity of the enzyme.

*Rhizopus, Talaromyces*, such as *Talaromyces emersoni* (dislosed in WO 99/28448), and *Thielavia* have high specific activity towards maltodextrins, including maltose and maltohepatose. Therefore, regions being of special interest are those involved in transferring specific activity.

The present inventors find that it is in fact possible to alter the thermal stability and/or to alter the specific activity of a parent glucoamylase by modification of one or more amino acid residues of the amino acid sequence of the parent glucoamylase. The present invention is based on this finding.

Accordingly, in a first aspect the present invention relates to an improved variant of a parent glucoamylase comprising one or more mutations in the regions and positions described further below.

Parent Glucoamylases

Parent glucoamylase contemplated according to the present invention include fungal glucoamylases, in particular fungal glucoamylases obtainable from an *Aspergillus* strain, such as an *Aspergillus niger* or *Aspergillus awamori* glucoamylases and variants or mutants thereof, homologous glucoamylases, and further glucoamylases being structurally and/or functionally similar to the amino acid sequence shown in SEQ ID NO: 2. Specifically contemplated are the *Aspergillus niger* glucoamylases G1 and G2 disclosed in Boel et al. (1984), "Glucoamylases G1 and G2 from *Aspergillus niger* are synthesized from two different but closely related mRNAs", EMBO J. 3 (5), p. 1097-1102. The G2 glucoamylase is disclosed as SEQ ID NO: 2. The G1 glucoamylase is disclosed as SEQ ID NO: 13. Another AMG backbone contemplated is *Talaromyces emersonii*, especially *Talaromyces emersonii* DSM disclosed in WO 99/28448 (Novo Nordisk).

Commercially Available Parent Glucoamylases

Commercially available parent glucoamylases include AMG from Novozymes, and also glucoamylase from the companies Genencor Int., Inc., USA, and Gist-Brocades (DSM), Delft, The Netherlands.

Glucoamylase Variants

In the first aspect the invention relates to a variant of a parent glucoamylase comprising one or more mutation(s) in position(s) or region(s) corresponding to the following position(s) or region(s) in the amino acid sequence published as SEQ ID NO: 2.

a) said variant comprising one or more insertion(s) in:
Region: 1-35, Region: 40-58, Region: 60-62, Region: 73-80, Position: 93, Region: 95-101, Region: 103-121, Region: 123-124, Region: 126-127, Region: 170-175, Region: 177-184, Region: 200-212, Region: 234-246, Region: 287-312, Region: 314-319, Region: 334-339, Position: 341, Region: 354-356, Position: 358, Region:

360-374, Region: 388-392, Position: 94, Region: 396-401, Region: 403-407, Region: 409-414, Region: 445-449, Region: 452-467, Region: 469-470, and/or in a corresponding position or region in a homologous glucoamylase which displays at least 60% homology with the amino acid sequences shown in SEQ ID NO: 2, or said variant comprising one or more substitution(s), insertion(s) and/or deletion(s) in: Region: 36-39, Region: 63-65, Position 67, Region: 69-71, Region: 81-92, Region: 128-169, Region: 85-188, Region: 190-199, Region: 213-222, Region: 224-226, Region: 228-233, Region: 247-271, Region: 273-286, Region: 320-333, Region: 343-344, Region: 346-347, Region: 349-351, Region: 375-378, Region: 380-385, Position: 387, Position: 415, Region: 417-424, Position: 426, Region: 428-443, Region: 471-485, Region: 487489, Region: 491-493, Region: 495-616, and/or in a corresponding position or region in a homologous glucoamylase which displays at least 60% homology with the amino acid sequence shown in SEQ ID NO: 2, except the following amino acid substitutions: A39V, P128S, G137A, G139A, D153N, S185H, G251A, D257E, E259D, E259Q, C320A, D375C, G383A, W417F, S431C, A435P, S436P, W437F, A442T, A471C, A479C, T480C, P481C, A495T and A495P.

In an embodiment, the region where one or more insertion(s) is made in the Region: 1-35. Specific preferred positions contemplated include one or more of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35.

In an embodiment, the region where one or more insertion(s) is made in the Region: 40-58. Specific preferred positions contemplated include one or more of: 40, 41, 42, 43, 44, 45, 46, 47, 49, 49, 50, 51, 52, 53, 54, 55, 56, 57, 58.

In an embodiment, the region where one or more insertion(s) is made in the Region: 60-62. Specific preferred positions contemplated include one or more of: 60, 61, 62.

In an embodiment, the region where one or more insertion(s) is made in the Region: 73-80.

Specific preferred positions contemplated include one or more of: 73, 74, 75, 76, 77, 78, 79, 80.

In an embodiment, the region where one or more insertion(s) is made in the Region: 95-101. Specific preferred positions contemplated include one or more of: 95, 96, 97, 98, 99, 100, 101.

In an embodiment, the region where one or more insertion(s) is made in the Region: 103-121. Specific preferred positions contemplated include one or more of: 103, 104, 105, 106, 107, 108, 109, 110, 111, 112, 113, 114, 115, 116, 117, 118, 119, 120, 121.

In an embodiment, the region where one or more insertion(s) is made in the Region: 123-124. Specific preferred positions contemplated include one or more of: 123, 124.

In an embodiment, the region where one or more insertion(s) is made in the Region: 126-127. Specific preferred positions contemplated include one or more of: 126, 127.

In an embodiment, the region where one or more insertion(s) is made in the Region: 170-175. Specific preferred positions contemplated include one or more of: 170, 171, 172, 173, 174, 175.

In an embodiment, the region where one or more insertion(s) is made in the Region: 177-184. Specific preferred positions contemplated include one or more of: 177, 178, 179, 180, 181, 182, 183, 184.

In an embodiment, the region where one or more insertion(s) is made in the Region: 200-212. Specific preferred positions contemplated include one or more of: 200, 201, 202, 203, 204, 205, 206, 207, 208, 209, 210, 211, 212.

In an embodiment, the region where one or more insertion(s) is made in the Region: 234-246. Specific preferred positions contemplated include one or more of: 234, 235, 236, 237, 238, 239, 240, 241, 242, 243, 244, 245, 246.

In an embodiment, the region where one or more insertion(s) is made in the Region: 287-312. Specific preferred positions contemplated include one or more of: 287, 288, 289, 290, 291, 292, 293, 294, 295, 296, 297, 298, 299, 300, 301, 302, 303, 304, 305, 306, 307, 308, 309, 310, 311, 312.

In an embodiment, the region where one or more insertion(s) is made in the Region: 314-319. Specific preferred positions contemplated include one or more of: 314, 315, 316, 317, 318, 319.

In an embodiment, the region where one or more insertion(s) is made in the Region: 334-339. Specific preferred positions contemplated include one or more of: 334, 335, 336, 337, 338, 339. Another specific preferred position is 341.

In an embodiment, the region where one or more insertion(s) is made in the Region: 354-356. Specific preferred positions contemplated include one or more of: 354, 355, 356. Another specific preferred position is 358.

In an embodiment, the region where one or more insertion(s) is made in the Region: 360-374. Specific preferred positions contemplated include one or more of: 360, 361, 362, 363, 364, 365, 366, 367, 368, 369, 370, 371, 372, 373, 374.

In an embodiment, the region where one or more insertion(s) is made in the Region: 388-392. Specific preferred positions contemplated include one or more of: 388, 389, 390, 391, 392. Another specific preferred position is 394.

In an embodiment, the region where one or more insertion(s) is made in the Region: 396-401. Specific preferred positions contemplated include one or more of: 396, 397, 398, 399, 400, 401.

In an embodiment, the region where one or more insertion(s) is made in the Region: 403-407. Specific preferred positions contemplated include one or more of: 403, 404, 405, 406, 407.

In an embodiment, the region where one or more insertion(s) is made in the Region: 409-414. Specific preferred positions contemplated include one or more of: 409, 410, 411, 412, 413, 414.

In an embodiment, the region where one or more insertion(s) is made in the Region: 445-449. Specific preferred positions contemplated include one or more of: 445, 446, 447, 448, 449.

In an embodiment, the region where one or more insertion(s) is made in the Region: 452-467. Specific preferred positions contemplated include one or more of: 452, 453, 454, 455, 456, 457, 458, 459, 460, 461, 462, 463, 464, 465, 466, 467.

In an embodiment, the region where one or more insertion(s) is made in the Region: 469-470. Specific preferred positions contemplated include one or more of: 469, 470.

In an embodiment, the region where one or more substitution(s), insertion(s) and/or deletion(s) is made is the Region: 36-39. Specific preferred positions contemplated include one or more of: 36, 37, 38, 39, except the amino acid substitution: A39V.

In an embodiment, the region where one or more substitution(s), insertion(s) and/or deletion(s) is made is the Region: 63-65. Specific preferred positions contemplated include one or more of: 63, 64, 65. Another specific preferred position is 67.

In an embodiment, the region where one or more substitution(s), insertion(s) and/or deletion(s) is made is the Region: 69-71. Specific preferred positions contemplated include one or more of: 69, 70, 71.

In an embodiment, the region where one or more substitution(s), insertion(s) and/or deletion(s) is made is the Region: 81-92. Specific preferred positions contemplated include one or more of: 81, 82, 83, 84, 85, 86, 87, 88, 89, 90, 91, 92.

In an embodiment, the region where one or more substitution(s), insertion(s) and/or deletion(s) is made is the Region: 128-169. Specific preferred positions contemplated include one or more of: 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, except the amino acid substitution(s) P128S, G137A, G139A, and D153N.

In an embodiment, the region where one or more substitution(s), insertion(s) and/or deletion(s) is made in the Region: 185-188. Specific preferred positions contemplated include one or more of: 185, 186, 187, 188, except the amino acid substitution(s) S185H.

In an embodiment, the region where one or more substitution(s), insertion(s) and/or deletion(s) is made in the Region: 190-199. Specific preferred positions contemplated include one or more of: 190, 191, 192, 193, 194, 195, 196, 197, 198, 199.

In an embodiment, the region where one or more substitution(s), insertion(s) and/or deletion(s) is made in the Region: 213-222. Specific preferred positions contemplated include one or more of: 213, 214, 215, 216, 217, 218, 219, 220, 221, 222.

In an embodiment, the region where one or more substitution(s), insertion(s) and/or deletion(s) is made in the Region: 224-226. Specific preferred positions contemplated include one or more of: 224, 225, 226.

In an embodiment, the region where one or more substitution(s), insertion(s) and/or deletion(s) is made in the Region: 228-233. Specific preferred positions contemplated include one or more of: 228, 229, 230, 231, 232, 233.

In an embodiment, the region where one or more substitution(s), insertion(s) and/or deletion(s) is made in the Region: 247-271. Specific preferred positions contemplated include one or more of: 247, 248, 249, 250, 251, 252, 253, 254, 255, 256, 257, 258, 259, 260, 261, 262, 263, 264, 265, 267, 268, 269, 270, 271, except the amino acid substitution(s) G251A, D257E, E259D, and E259Q.

In an embodiment, the region where one or more substitution(s), insertion(s) and/or deletion(s) is made in the Region: 273-286. Specific preferred positions contemplated include one or more of: 273, 274, 275, 276, 277, 278, 279, 280, 281, 282, 283, 284, 285, 286.

In an embodiment, the region where one or more substitution(s), insertion(s) and/or deletion(s) is made in the Region: 320-333. Specific preferred positions contemplated include one or more of: 320, 321, 322, 323, 324, 325, 326, 327, 328, 329, 330, 331, 332, 333, except the amino acid substitution(s) C320A.

In an embodiment, the region where one or more substitution(s), insertion(s) and/or deletion(s) is made in the Region: 343-244. Specific preferred positions contemplated include one or more of: 343, 344.

In an embodiment, the region where one or more substitution(s), insertion(s) and/or deletion(s) is made in the Region: 346-347. Specific preferred positions contemplated include one or more of: 346, 347.

In an embodiment, the region where one or more substitution(s), insertion(s) and/or deletion(s) is made in the Region: 349-351. Specific preferred positions contemplated include one or more of: 349, 350, 351.

In an embodiment, the region where one or more substitution(s), insertion(s) and/or deletion(s) is made in the Region: 375-378. Specific preferred positions contemplated include one or more of: 375, 376, 377, 378, except the amino acid substitution(s) D375C.

In an embodiment, the region where one or more substitution(s), insertion(s) and/or deletion(s) is made in the Region: 380-385. Specific preferred positions contemplated include one or more of: 380, 381, 382, 383, 384, 385, except the amino acid substitution(s) G383A. Other specific preferred positions contemplated include: 387, 415.

In an embodiment, the region where one or more substitution(s), insertion(s) and/or deletion(s) is made in the Region: 417-424. Specific preferred positions contemplated include one or more of: 417, 418, 419, 420, 421, 422, 423, 424, except the amino acid substitution(s) W417F. Another specific preferred position contemplated includes: 426.

In an embodiment, the region where one or more substitution(s), insertion(s) and/or deletion(s) is made in the Region: 428-443. Specific preferred positions contemplated include one or more of: 428, 429, 430, 431, 432, 433, 434, 435, 436, 437, 438, 439, 440, 441, 442, 443, except the amino acid substitution(s) S431C, A435P, S436P, W437F, A442T.

In an embodiment, the region where one or more substitution(s), insertion(s) and/or deletion(s) is made in the Region: 471-485. Specific preferred positions contemplated include one or more of: 471, 472, 473, 474, 475, 476, 477, 478, 479, 480, 481, 482, 483, 484, 485, except the amino acid substitution(s) A471C, A479C, T480C, P481C.

In an embodiment, the region where one or more substitution(s), insertion(s) and/or deletion(s) is made in the Region: 487489. Specific preferred positions contemplated include one or more of: 487, 488, 489.

In an embodiment, the region where one or more substitution(s), insertion(s) and/or deletion(s) is made in the Region: 491493. Specific preferred positions contemplated include one or more of: 491, 492, 493.

In an embodiment, the region where one or more substitution(s), insertion(s) and/or deletion(s) is made in the Region: 495-616. Specific preferred positions contemplated include one or more of: 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, except the amino acid substitution(s) A495T and A495P.

In a second aspect of the invention relates to a DNA construct comprising a DNA sequence encoding a glucoamylase variant of the first aspect.

A third aspect of the invention relates to a recombinant expression vector which carries a DNA construct according to the second aspect and as defined elsewhere herein.

A fourth aspect relates to a cell which is transformed with a DNA construct according to the second aspect or a vector according to the third aspect.

In a fifth aspect the invention relates to a cell according to the fourth aspect, which is a microorganism, such as a bacterium or a fungus. A preferred embodiment relates to a cell of this aspect, which is a protease deficient *Aspergillus oryzae* or *Aspergillus niger*.

A sixth aspect relates to a process for converting starch or partially hydrolyzed starch into a syrup containing dextrose, said process including the step saccharifying starch hydrolyzate in the presence of a glucoamylase variant according to the first aspect. Preferably the dosage of glucoamylase is present in the range from 0.05 to 0.5 AGU per gram of dry solids. In a preferred embodiment of this aspect the process comprises saccharification of a starch hydrolyzate of at least 30 percent by weight of dry solids. In another preferred embodiment, the saccharification is conducted in the presence of a debranching enzyme selected from the group of pullulanase and isoamylase, preferably a pullulanase derived from *Bacillus acidopullulyticus* or *Bacillus deramificans* or an isoamylase derived from *Pseudomonas amyloderamosa*. Still in another embodiment, the saccharification is conducted at a pH of 3 to 5.5 and at a temperature of 60-80° C., preferably 63-75° C., for 24 to 72 hours, preferably for 36-48 hours at a pH from 4 to 4.5.

A seventh aspect relates to a method of saccharifying a liquefied starch solution, which method comprises:
  (i) a saccharification wherein one or more enzymatic saccharification stages takes place, and
  (ii) one or more high temperature membrane separation steps, wherein the enzymatic saccharification is carried out using a glucoamylase variant according to the first aspect.

Several aspects of the invention relate to uses of a glucoamylase variant according to the first aspect, such as the use in a starch conversion process; the use in a continuous starch conversion process, preferably wherein the continuous starch conversion process include a continuous saccharification process according to the seventh aspect; the use in a process for producing oligosaccharides; the use in a process for producing specialty syrups; the use in a process for producing ethanol for fuel; the use in a process for producing a beverage; and finally the use in a fermentation process for producing organic compounds, such as citric acid, ascorbic acid, lysine, glutamic acid.

A final aspect of the invention relates to a method for altering the thermostability and/or of altering the specific activity of a parent glucoamylase by making one or more mutation(s) in one or more of the following position(s) or region(s) corresponding to the position(s) or region(s) of the amino acid sequence shown in NO: 2:

a) said mutation(s) comprising one or more insertion(s) in: Region: 1-35, Region: 40-58, Region: 60-62, Region: 73-80, Position: 93, Region: 95-101, Region: 103-121, Region: 123-124, Region: 126-127, Region: 170-175, Region: 177-184, Region: 200-212, Region: 234-246, Region: 287-312, Region: 314-319, Region: 334-339, Position: 341, Region: 354-356, Position: 358, Region: 360-374, Region: 388-392, Position: 94, Region: 396-401, Region: 403-407, Region: 409-414, Region: 445-449, Region: 452-467, Region: 469-470, and/or in a corresponding position or region in a homologous glucoamylase which displays at least 60% homology with the amino acid sequences shown in SEQ ID NO: 2, or b) said mutation(s) comprising one or more substitution(s), insertion(s) and/or deletion(s) in: Region: 36-39, Region: 63-65, Position 67, Region: 69-71, Region: 81-92, Region: 128-169, Region: 85-188, Region: 190-199, Region: 213-222, Region: 224-226, Region: 228-233, Region: 247-271, Region: 273-286, Region: 320-333, Region: 343-344, Region: 346-347, Region: 349-351, Region: 375-378, Region: 380-385, Position: 387, Position: 415, Region: 417-424, Position: 426, Region: 428443, Region: 471-485, Region: 487-489, Region: 491-493, Region: 495-616, and/or in a corresponding position or region in a homologous glucoamylase which displays at least 60% homology with the amino acid sequence shown in SEQ ID NO: 2 of WO 00/04136, except the following amino acid substitutions: A39V, P128S, G137A, G139A, D153N, S185H, G251A, D257E, E259D, E259Q, C320A, D375C, G383A, W417F, S431C, A435P, S436P, W437F, A442T, A471C, A479C, T480C, P481C, A495T and A495P.

Preferred embodiments of the final aspect are identical to those of the first aspect and relate to one or more mutation(s) in specific position(s) corresponding to specific position(s) of SEQ ID NO: 2, as shown above.

Homology (Identity)

The homology referred to above of the parent glucoamylase is determined as the degree of identity between two protein sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443-453). Using Gap with the following settings for polypeptide sequence comparison: Gap creation penalty of 3.0 and Gap extension penalty of 0.1, the mature part of a polypeptide encoded by an analogous DNA sequence of the invention exhibits a degree of identity preferably of at least 60%, such as 70%, at least 80%, at least 90%, more preferably at least 95%, more preferably at least 97%, and most preferably at least 99% with the mature part of the amino acid sequence shown in SEQ ID NO: 2.

Preferably, the parent glucoamylase comprise the amino acid sequences of SEQ ID NO: 2; or allelic variants thereof; or fragments thereof that have glucoamylase activity.

A fragment of the amino acid sequence shown in SEQ ID NO: 2 is a polypeptide which has one or more amino acids deleted from the amino and/or carboxyl terminus of this amino acid sequence. For instance, the AMG G2 (SEQ ID NO: 2 is a fragment of the *Aspergillus niger* G1 glucoamylase (Boel et al. (1984), EMBO J. 3 (5), p. 1097-1102) having glucoamylase activity. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of homologous parent glucoamylases may differ from the amino acid sequence of SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the isolated parent glucoamylase is encoded by a nucleic acid sequence which hybridises under very low stringency conditions, preferably low stringency conditions, more preferably medium stringency conditions, more preferably medium-high stringency conditions, even more preferably high stringency conditions, and most preferably very high stringency conditions with a nucleic acid probe which hybridises under the same conditions with (i) the nucleic acid sequence of SEQ ID NO: 1, (ii) the cDNA sequence of SEQ ID NO:1, (iii) a sub-sequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The sub-sequence of SEQ ID NO: 1 may be at least 100 nucleotides or preferably at least 200 nucleotides. Moreover, the sub-sequence may encode a polypeptide fragment which has glucoamylase activity. The parent polypeptides may also be allelic variants or fragments of the polypeptides that have glucoamylase activity.

The nucleic acid sequence of SEQ ID NO: 1 or a subsequence thereof, as well as the amino acid sequence of SEQ ID NO: 2, or a fragment thereof, may be used to design a nucleic acid probe to identify and clone DNA encoding polypeptides having glucoamylase activity, from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and which encodes a polypeptide having glucoamylase. Genomic or other DNA from such other organisms may be separated by agarose or polyacrylamide gel electrophoresis, or other separation techniques. DNA from the libraries or the separated DNA may be transferred to and immobilised on nitrocellulose or other suitable carrier material. In order to identify a clone or DNA that is homologous with SEQ ID NO: 1, or sub-sequences thereof, the carrier material is used in a Southern blot. For purposes of the present invention, hybridisation indicates that the nucleic acid sequence hybridises to a nucleic acid probe corresponding to the nucleic acid sequence shown in SEQ ID NO: 1, its complementary strand, or a sub-sequence thereof, under very low to very high stringency conditions. Molecules to which the nucleic acid probe hybridises under these conditions are detected using X-ray film.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridisation, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes, which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridising a DNA under very low, low, medium, medium-high, high, or very high stringency conditions with the sequence of SEQ ID NO:1, or its complementary strand, or a sub-sequence thereof; and (b) isolating the nucleic acid sequence. The sub-sequence is preferably a sequence of at least 100 nucleotides such as a sequence, which encodes a polypeptide fragment, which has glucoamylase activity.

Contemplated parent glucoamylases have at least 20%, preferably at least 40%, more preferably at least 60%, even more preferably at least 80%, even more preferably at least 90%, and most preferably at least 100% of the glucoamylase activity of the mature polypeptide of SEQ ID NO: 2.

In a preferred embodiment the variant of the invention has improved thermal stability and/or increased specific activity, preferably within the temperature interval from about 60-80° C., preferably 63-75° C., preferably at a pH of 4-5, in particular 4.24.7, using maltodextrin as the substrate.

In another preferred embodiment a variant of the invention is used for, e.g., alcohol fermentation.

In a preferred embodiment the parent glucoamylase is the *Aspergillus niger* G1 glucoamylase (Boel et al. (1984), EMBO J. 3 (5), p. 1097-1102. The parent glucoamylase may be a truncated glucoamylase, e.g., the AMG G2 glucoamylase.

Cloning a DNA Sequence Encoding a Parent Glucoamylase

The DNA sequence encoding a parent glucoamylase may be isolated from any cell or microorganism producing the glucoamylase in question, using various methods well known in the art. First, a genomic DNA and/or cDNA library should be constructed using chromosomal DNA or messenger RNA from the organism that produces the glucoamylase to be studied. Then, if the amino acid sequence of the glucoamylase is known, labeled oligonucleotide probes may be synthesized and used to identify glucoamylase-encoding clones from a genomic library prepared from the organism in question. Alternatively, a labelled oligonucleotide probe containing sequences homologous to another known glucoamylase gene could be used as a probe to identify glucoamylase-encoding clones, using hybridization and washing conditions of very low to very high stringency. This is described above.

Yet another method for identifying glucoamylase-encoding clones would involve inserting fragments of genomic DNA into an expression vector, such as a plasmid, transforming glucoamylase-negative bacteria with the resulting genomic DNA library, and then plating the transformed bacteria onto agar containing a substrate for glucoamylase (i.e., maltose), thereby allowing clones expressing the glucoamylase to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), *Science* 239, 1988, pp. 487-491.

Site-Directed Mutagenesis

Once a glucoamylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the glucoamylase-encoding sequence, is created in a vector carrying the glucoamylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into glucoamylase-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Further, Sierks. et al., (1989), Protein Eng., 2, 621-625; Sierks et al., (1990), Protein Eng. vol. 3, 193-198; also describes site-directed mutagenesis in an *Aspergillus* glucoamylase.

Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent glucoamylase may be conveniently performed by use of any method known in the art.

In relation to the above, a further aspect of the present invention relates to a method for generating a variant of a parent glucoamylase, wherein the variant exhibits increased thermal stability relative to the parent, the method comprising:

(a) subjecting a DNA sequence encoding the parent glucoamylase to random mutagenesis, (b) expressing the mutated DNA sequence obtained in step (a) in a host cell, and (c) screening for host cells expressing a glucoamylase variant which has an altered property (i.e. thermal stability) relative to the parent glucoamylase.

Step (a) of the above method of the invention is preferably performed using doped primers, as described in the working examples herein (vide infra).

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the glucoamylase enzyme by any published technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent glucoamylase is subjected to PCR under conditions that increase the mis-incorporation of nucleotides (Deshler 1992; Leung et al., Technique, Vol.1, 1989, pp. 11-15).

A mutator strain of *E. coli* (Fowler et al., Molec. Gen. Genet., 133, 1974, pp. 179-191), *S. cereviseae* or any other microbial organism may be used for the random mutagenesis of the DNA encoding the glucoamylase by, e.g., transforming a plasmid containing the parent glycosylase into the mutator strain, growing the mutator strain with the plasmid and isolating the mutated plasmid from the mutator strain. The mu-ta-ted plasmid may be subsequently transformed into the expression organism.

The DNA sequence to be mutagenized may be conveniently present in a genomic or cDNA library prepared from an organism expressing the parent glucoamylase. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent glucoamylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative methods for providing variants of the invention include gene shuffling e.g. as described in WO 95/22625 (from Affymax Technologies N.V.) or in WO 96/00343 (from Novo Nordisk A/S).

Expression of Glucoamylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a glucoamylase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell.

Examples of suitable promoters for directing the transcription of the DNA sequence encoding a glucoamylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question.

Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a glucoamylase variant, the promoter, terminator and other elements, respectively, and to insert them into suitable vectors containing the information necessary for replication, are well known to persons skilled in the art (cf., for instance, Sambrook et al., *Molecular Cloning: A Laboratory Manual*, 2nd Ed., Cold Spring Harbor, 1989).

Host Cells

The cell of the invention, either comprising a DNA construct or an expression vector of the invention as defined above, is advantageously used as a host cell in the recombinant production of a glucoamylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*.

The host cell may also be a filamentous fungus e.g. a strain belonging to a species of *Aspergillus*, most preferably *Aspergillus oryzae* or *Aspergillus niger*, or a strain of *Fusarium*, such as a strain of *Fusarium oxysporium, Fusarium graminearum* (in the perfect state named *Gribberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucium, Fusarium roseum*, and *Fusarium roseum* var. *graminearum*), *Fusarium cerealis* (synonym with *Fusarium crokkwellnse*), or *Fusarium venenatum.*

In a preferred embodiment of the invention the host cell is a protease deficient or protease minus strain.

This may for instance be the protease deficient strain *Aspergillus oryzae* JaL125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host micro-organism is described in EP 238 023 (Novo Nordisk AIS), the contents of which are hereby incorporated by reference.

Method of Producing a Glucoamylase Variant

In a yet further aspect, the present invention relates to a method of producing a glucoamylase variant of the invention, which method comprises cultivating a host cell under conditions conducive to the production of the variant and recovering the variant from the cells and/or culture medium.

The medium used to cultivate the cells may be any conventional medium suitable for growing the host cell in question and obtaining expression of the glucoamylase variant of the invention. Suitable media are available from commercial suppliers or may be prepared according to published recipes (e.g. as described in catalogues of the American Type Culture Collection).

The glucoamylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Starch Conversion

The present invention provides a method of using glucoamylase variants of the invention for producing glucose and the like from starch. Generally, the method includes the steps of partially hydrolyzing precursor starch in the presence of alpha-amylase and then further hydrolyzing the release of D-glucose from the non-reducing ends of the starch or related oligo- and polysaccharide molecules in the presence of glucoamylase by cleaving alpha-(1→4) and alpha-(1→6) glucosidic bonds.

The partial hydrolysis of the precursor starch utilizing alpha-amylase provides an initial breakdown of the starch molecules by hydrolyzing internal alpha-(1→4)-linkages. In commercial applications, the initial hydrolysis using alpha-amylase is run at a temperature of approximately 105° C. A very high starch concentration is processed, usually 30% to 40% solids. The initial hydrolysis is usually carried out for five minutes at this elevated temperature. The partially hydrolyzed starch can then be transferred to a second tank and incubated for approximately 1-2 hour at a temperature of 85° to 98° C. to derive a dextrose equivalent (D.E.) of 10 to 15.

The step of further hydrolyzing the release of D-glucose from the non-reducing ends of the starch or related oligo- and polysaccharides molecules in the presence of glucoamylase is normally carried out in a separate tank at a reduced temperature between 30° and 62° C. Preferably the temperature of the substrate liquid is dropped to between 550 and 60° C. The pH of the solution is dropped from about 5.5 to 6.5 to a range between 3 and 5.5. Preferably, the pH of the solution is 4 to 4.5. The glucoamylase is added to the solution and the reaction is carried out for 24-72 hours, preferably 3648 hours.

By using a thermostable glucoamylase variant of the invention saccharification processes may be carried out at a higher temperature than traditional batch saccharification processes. According to the invention saccharification may be carried out at temperatures in the range from above 60-80° C., preferably 63-75° C. This apply both for traditional batch processes (described above) and for continuous saccharification processes.

Actually, continuous saccharification processes including one or more membrane separation steps, i.e. filtration steps, must be carried out at temperatures of above 60° C. to be able to maintain a reasonably high flux over the membrane or to minimize microbial contamination. Therefore, the thermostable variants of the invention provides the possibility of carrying out large scale continuous saccharification processes at a fair price and/or at a lower enzyme protein dosage within a period of time acceptable for industrial saccharification processes. According to the invention the saccharification time may even be shortened.

The activity of the glucoamylase variant (e.g. AMG variant) of the invention is generally substantially higher at temperatures between 60° C.-80° C. than at the traditionally used temperature between 30-60° C. Therefore, by increasing the temperature at which the glucoamylase operates the saccharification process may be carried out within a shorter period of time.

Further, by improving the thermal stability the $T_{1/2}$ (half-time, as defined in the "Materials and Methods" section) is improved. As the thermal stability of the glucoamylase variants of the invention is improved a minor amount of glucoamylase need to be added to replace the glucoamylase being inactivated during the saccharification process. More glucoamylase is maintained active during saccharification process according to the present invention. Furthermore, the risk of microbial contamination is also reduced when carrying the saccharification process at temperature above 63° C.

The glucose yield from a typical saccharification trial with glucoamylase, acid amylase and pullulanase is 95.5-96.5%. The remaining carbohydrates typically consists of 1% maltose, 1.5-2% isomaltose and 1-1.5% higher oligosacharides. The disaccharides are produced since the glucoamylase at high concentrations of glucose and high dry-solid levels has a tendency to form reversion products.

A glucoamylase with an increased specific activity towards saccharides present in the solution after liquefaction and saccharides formed during saccharification would be an advantage as a reduced enzyme protein dosage or a shorter process time then could be used. In general, the glucoamylase has a preference for substrates consisting of longer saccharides compared to short chain saccharides and the specific activity towards e.g. maltoheptaose is therefore approximately 6 times higher than towards maltose. An increased specific activity towards short chain saccharides such as maltose (without reducing the activity towards oligosaccharides) would therefore also permit using a lower enzyme dosage and/or shorter process time.

Furthermore, a higher glucose yield can be obtained with a glucoamylase variant with an increased alpha-1,4 hydrolytic activity (if the alpha-1,6 activity is unchanged or even decreased), since a reduced amount of enzyme protein is being used, and alpha-1,6 reversion product formation therefore is decreased (less isomaltose).

The specific activity may be measured using the method described in the "Materials & Methods" section at 37° C. or 60° C.

Example of saccharification process wherein the glucoamylase variants of the invention may be used include the processes described in JP 3-224493; JP 1-191693; JP 62-272987; EP 452,238, and WO 99/27124 (all references are hereby incorporated by reference).

In a further aspect the invention relates to a method of saccharifying a liquefied starch solution, comprising the steps
(i) a saccharification step during which step one or more enzymatic saccharification stages takes place, and the subsequent step of
(ii) one or more high temperature membrane separation steps wherein the enzymatic saccharification is carried out using a thermostable glucoamylase variant of the invention.

The glucoamylase variant(s) of the invention may be used in the present inventive process in combination with an enzyme that hydrolyzes only α-(1→6)-glucosidic bonds in molecules with at least four glucosyl residues. Preferentially, the glucoamylase variant of the invention can be used in combination with pullulanase or isoamylase. The use of isoamylase and pullulanase for debranching, the molecular properties of the enzymes, and the potential use of the enzymes with glucoamylase is set forth in G. M. A. van Beynum et al., Starch Conversion Technology, Marcel Dekker, New York, 1985, 101-142.

In a further aspect the invention relates to the use of a glucoamylase variant of the invention in a starch conversion process.

Further, the glucoamylase variant of the invention may be used in a continuous starch conversion process including a continuous saccharification step.

The glucoamylase variants of the invention may also be used in immobilised form. This is suitable and often used for producing speciality syrups, such as maltose syrups, and further for the raffinate stream of oligosaccharides in connection with the production of fructose syrups.

The glucoamylase of the invention may also be used in a process for producing ethanol for fuel or beverage or may be used in a fermentation process for producing organic compounds, such as citric acid, ascorbic acid, lysine, glutamic acid.

MATERIALS & METHODS

MATERIALS

Enzymes:
AMG G1: *Aspergillus niger* glucoamylase G1 disclosed in Boel et al. (1984), *EMBO J.* 3 (5), 1097-1102, and SEQ ID NO: 13, available from Novo Nordisk.

AMG G2: Truncated *Aspergillus niger* glucoamylase G1 shown in SEQ ID NO: 2 (available from Novo Nordisk)

Solutions:
Buffer: 0.05M sodium acetate (6.8 g in 1 l milli-Q-water), pH 4.5
Stop solution: 0.4M NaOH
GOD-perid, 124036, Boehringer Mannheim Substrate:

Maltose: 29 mM (1g maltose in 100 ml 50 mM sodium acetate, pH 4.5) (Sigma)

Maltoheptaose: 10 mM, 115 mg/10 ml (Sigma)

Host Cell:

A. oryzae JaL 125: *Aspergillus oryzae* IFO 4177 available from Institute for Fermention, Osaka; 17-25 Juso Hammachi 2-Chome Yodogawa-ku, Osaka, Japan, having the alkaline protease gene named "alp" (described by Murakami K et al., (1991), *Agric. Biol. Chem.* 55, p. 2807-2811) deleted by a one step gene replacement method (described by G. May in "Applied Molecular Genetics of Filamentous Fungi" (1992), p. 1-25. Eds. J. R. Kinghom and G. Turner; Blackie Academic and Professional), using the *A. oryzae* pyrG gene as marker. Strain JaL 125 is further disclosed in WO 97/35956 (Novo Nordisk).

Microorganisms:

Strain: *Saccharomyces cerevisiae* YNG318: MATαleu2-Δ2 ura3-52 his4-539 pep4-Δ1 [cir+]

Plasmids:

pCAMG91: See FIG. 1 of WO 00/04136. Plasmid comprising the *Aspergillus niger* G1 glucoamylase (AMG G1). The construction of pCAMG91 is described in Boel et al. (1984), EMBO J. 3 (7) p.1581-1585.

pMT838: Plasmid encoding the truncated *Aspergillus niger* glucoamylase G2 (SEQ ID NO: 2).

pJSO026 (*S. cerevisiae* expression plasmid) (J. S. Okkels, (1996) "A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences) More specifically, the expression plasmid pJSO37, is derived from pYES 2.0 by replacing the inducible GALL-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419-434), and deleting a part of the URA3 promoter.

METHODS

Transformation of *Saccharomyces cerevisiae* YNG318

The DNA fragments and the opened vectors are mixed and transformed into the yeast 30 *Saccharomyces cerevisiae* YNG318 by standard methods.

Determining Specific Activity as $k_{cat}$ (sec.$^{-1}$).

750 microL substrate (1% maltose, 50 mM Sodium acetat, pH 4.3) is incubated 5 minutes at selected temperature, such as 37° C. or 60° C.

50 microL enzyme diluted in sodium acetate is added.

Aliquots of 100 microL are removed after 0, 3, 6, 9 and 12 minutes and transferred to 100 microL 0.4 M Sodium hydroxide to stop the reaction. A blank is included.

20 microL is transferred to a Micro titre plates and 200 microL GOD-Perid solution is added. Absorbance is measured at 650 nm after 30 minutes incubation at room temperature.

Glucose is used as standard and the specific activity is calculated as $k_{cat}$ (sec.$^{-1}$).

Determination of AGU Activity and as AGU/mg

One Novo Amyloglucosidase Unit (AGU) is defined as the amount of enzyme which hydrolyzes 1 micromole maltose per minute at 37° C. and pH 4.3. A detailed description of the analytical method (AEL-SM-0131) is available on request from Novo Nordisk.

The activity is determined as AGU/ml by a method modified after (AEL-SM-0131) using the Glucose GOD-Perid kit from Boehringer Mannheim, 124036. Standard: AMG-standard, batch 7-1195, 195 AGU/ml.

375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution is added. After 30 minutes at room temperature, the absorbance is measured at 650 nm and the activity calculated in AGU/ml from the AMG-standard.

The specific activity in AGU/mg is then calculated from the activity (AGU/ml) divided with the protein concentration (mg/ml).

Transformation of *Aspergillus oryzae* (General Procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M MgSO$_4$. The mycelium is suspended in 15 ml of 1.2 M MgSO$_4$, 10 mM NaH$_2$PO$_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5-2.5 hours at 37 C until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the MgSO$_4$ cushion. 2 volumes of STC (1.2 M sorbitol, 10 mM Tris-HCl, pH 7.5, 10 mM CaCl$_2$) are added to the protoplast suspension and the mixture is centrifugated for 5 min. at 1000 g. The protoplast pellet is resuspended in 3 ml of STC and repelleted. This is repeated. Finally, the protoplasts are resuspended in 0.2-1 ml of STC. 100 microL of protoplast suspension are mixed with 5-25 µg of p3SR2 (an *A. nidulans* amdS gene carrying plasmid described in Hynes et al., Mol. and Cel. Biol., Vol. 3, No. 8, 1430-1439, August 1983) in 10 microL of STC. The mixture is left at room temperature for 25 min. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2 M sorbitol. After one more sedimentation the protoplasts are spread on minimal plates (Cove, (1966), Biochem. Biophys. Acta 113, 51-56) containing 1.0 M sucrose, pH 7.0, 10 mM acetamide as nitrogen source and 20 mM CsCl to inhibit background growth. After incubation for 4-7 days at 37° C. spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, dear filtration and germ filtration.

Purification

The culture broth is filtrated and added ammoniumsulphate (AMS) to a concentration of 1.7 M AMS and pH is adjusted to pH 5. Precipitated material is removed by centrifugation and the solution containing glucoamylase activity is applied on a Toyo Pearl Butyl column previously equilibrated in 1.7 M AMS, 20 mM sodium acetate, pH 5. Unbound material is washed out with the equilibration buffer. Bound proteins are eluted with 10 mM sodium acetate, pH 4.5 using a linear gradient from 1.7-0 M AMS over 10 column volumes. Glucoamylase containing fractions are collected and dialysed against 20 mM sodium acetate, pH 4.5. The solution was then applied on a Q sepharose column, previously equilibrated in 10 mM piperazin, Sigma, pH 5.5. Unbound material is washed out with the equilibration buffer. Bound proteins are eluted with a linear gradient of 0-0.3 M Sodium chloride in 10 mM piperazin, pH 5.5 over 10 column volumes. Glucoamylase containing fractions are collected and the purity was confirmed by SDS-PAGE.

Construction of pAMGY

The pAMGY vector was constructed as follows: The lipase gene in pJSO026 was replaced by the AMG gene, which was PCR amplified with the forward primer; FG2: 5'-CAT CCC CAG GAT CCT TAC TCA GCA ATG-3' and the reverse primer RG2: 5'-CTC AAA CGA CTC ACC AGC CTC TAG AGT-3' using the template plasmid pLAC103 containing the AMG gene. The pJSO026 plasmid was digested with XbaI and SmaI at 37° C. for 2 hours and the PCR amplicon was blunt ended using the Klenow fragment and then digested with XbaI. The vector fragment and the PCR amplicon were ligated and transformed into *E. coli* by electrotransformation. The resulting vector is designated pAMGY.

Construction of pLaC103

The *A. niger* AMGII cDNA clone (Boel et al., (1984), supra) is used as source for the construction of pLaC103 aimed at *S. cerevisiae* expression of the GII form of AMG. The construction takes place In several steps, outlined below.

pT7-212 (EP37856/U.S. Pat. No. 5,162,498) is cleaved with XbaI, blunt-ended with Klenow DNA polymerase and dNTP. After cleavage with EcoRI the resulting vector fragment is purified from an agarose gel-electrophoresis and ligated with the 2.05 kb EcoR1-EcoRV fragment of pBoel53, thereby recreating the XbaI site in the EcoRV end of the AMG encoding fragment in the resulting plasmid pG2x.

In order to remove DNA upstream of the AMG cds, and furnish the AMG encoding DNA with an appropriate restriction endonuclease recognition site, the following construct was made:

The 930 bp EcoRI-PstI fragment of p53 was isolated and subjected to AluI cleavage, the resulting 771 bp Alu-PstI fragment was ligated into pBR322 with blunt-ended EcoRI site (see above) and cleaved with PstI In the resulting plasmid pBR-AMG', the EcoRI site was recreated just 34 bp from the initiation codon of the AMG cds.

From pBR-AMG' the 775 bp EcoRI-PstI fragment was isolated and joined with the 1151 bp PstI-XbaI fragment from pG2x in a ligation reaction including the XbaI-EcoRI vector fragment of pT7-212.

The resulting plasmid pT7GII was submitted to a BamHI cleavage in presence of alkaline phosphatase followed by partial SphI cleavage after inactivation of the phosphatase. From this reaction was the 2489 bp SphI-BamHI fragment, encompassing the S.c. TPI promoter linked to the AMGII cds.

The above fragment together with the 1052 bp BamHI fragment of pT7GII was ligated with the alkaline phosphatase treated vector fragment of pMT743 (EP37856/U.S. Pat. No. 5,162,498), resulting from SphI-BamHI digestion. The resulting plasmid is pLaC103.

Screening for Thermostable AMG Variants

The libraries are screened in the Filter Assay for Thermostability as described in WO 00/04136.

General Method for Random Mutagenesis by Use of the DOPE Program

The random mutagenesis may be carried out by the following steps:
1. Select regions of interest for modification in the parent enzyme,
2. Decide on mutation sites and non-mutated sites in the selected region,
3. Decide on which kind of mutations should be carried out, e.g., with respect to the desired stability and/or performance of the variant to be constructed,
4. Select structurally reasonable mutations,
5. Adjust the residues selected by step 3 with regard to step 4.
6. Analyze by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting glucoamylase variants by screening for the desired improved properties.

Dope Algorithm

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

Method Of Extracting Important Regions For Temperature Activity Using Molecular Simulation.

The X-ray structure and/or the model-build structure of the enzyme of interest, here AMG, are subjected to molecular dynamics simulations. The molecular dynamics simulation are made using the CHARMM (from Molecular simulations (MSI)) program or other suitable programs, e.g., DISCOVER (from MSI). The dynamics are made in vacuum, or including crystal waters, or with the enzyme in question embedded in a suitable waters, e.g., a sphere or a box. The simulation are run for 300 picoseconds (ps) or more, e.g., 300-1200 ps. The isotropic fluctuations are extracted for the CA carbons of the structures and comparison between the structures are made. More details on how to get the isotropic fluctuations can be found in the CHARMM manual (available from MSI) and hereby incorporated herein by reference. The molecular dynamics simulation can be carried out using standard charges on the chargeable amino acids. For instance, Asp and Glu is negatively charged and Lys and Arg are positively charged. This condition resembles the medium pH of approximately 7.0. To analyze a lower pH, titration of the molecule can be done to obtain the altered pKa's of the normal titrateable residues within pH 2-10; Lys, Arg, Asp, Glu, Tyr and His. Also Ser, Thr and Cys are titrateable but are not taking into account here. Here the altered charges due to the pH has been described as all Arg, Lys negative at high pH, and all Asp, Glu are uncharged. This imitates a pH around 4 to 5 where the titration Asp and Glu normally takes place. Model building of the enzyme of interest can be obtained by using the HOMOLOGY model in the MSI program package. The crystal structure of *Aspergillus awamori* variant X100 can be found in, e.g., 3GLY and 1DOG in the Brookhaven database.

EXAMPLES

Example 1

Construction of AMG G2 Variants

Site-Directed Mutagenesis:

For the construction of variants of AMG G2 (SEQ ID NO: 2 of WO 00/04136, available from Novo Nordisk) the commercial kit, Chameleon double-stranded, site-directed mutagenesis kit was used according to the manufacturer's instructions. The gene encoding the AMG G2 enzyme in question is located on pMT838 prepared by deleting the DNA between G2 nt. 1362 and G2 nt. 1530 in plasmid pCAMG91 comprising the AMG G1 form.

In accordance with the manufacturer's instructions the ScaI site of the Ampicillin gene of pMT838 was changed to a MluI site by use of the following primer:

Primer 7258: 5'p gaa tga ctt ggt tga cgc gtc acc agt cac (SEQ ID NO: 4)

(Thus changing the ScaI site found in the ampicillin resistance gene and used for cutting to a MluI site). The pMT838 vector comprising the AMG gene in question was then used as a template for DNA polymerase and primer 7258 (SEQ ID NO: 4) and primer 21401 (SEQ ID NO: 3). Primer 21401 (SEQ ID NO: 3) was used as the selection primer.

Primer 21401: 5'p gg gga tca tga tag gac tag cca tat taa tga agg gca tat acc acg cct tgg acc tgc gtt ata gcc (SEQ ID NO: 3)

(Changes the ScaI site found in the AMG gene without changing the amino acid sequence). The desired mutation (e.g., the introduction of a cystein residue) is introduced into the AMG gene in question by addition of appropriate oligos comprising the desired mutation. The primer 107581 was used to introduce T12P Primer 107581: 5' pgc aac gaa gcg ccc gtg gct cgt ac (SEQ ID NO: 4).

The mutations are verified by sequencing the whole gene. The plasmid was transformed into *A. oryzae* using the method described above in the "Materials & Methods" section. The variant was fermented and purified as described above in the "Materials & Methods" section.

Example 2

To improve the thermostability of the *A. niger* AMG, random mutagenesis in pre-selected region(s) was performed as shown in Example 2 of WO 00/04136 which is incorporated herein by reference. Construction was done by localized random, doped mutagenesis, of *A. niger* AMG resulting in variants having altered thermostability compared to the parent AMG enzyme.

Example 3

*A. niger* AMG variants having improved thermostability compared to the parent enzyme. Construction, by PCR shuffling spiked with DNA oligos, was performed as described in 15 Example 3 of WO 00/04136, which is incorporated herein by reference.

Example 4

Specific Activity

AMG G2 variants were constructed as described above in Example 1. The specific activity as $k_{cat}$ were measured on purified samples at pH 4.3, 37° C., using maltose and maltohepatose as substrate as described in the "Materials & Methods" section above. The specific activity as AGU/mg were also measured at pH 4.3, 37° C., using maltose as substrate as described in the "Materials & Methods" section above.

|  | Kcat (sec.-1) | |
| --- | --- | --- |
| Variant | Maltose | Maltoheptaose |
| AMG G2 (wt) | 6.0 | 38 |
| N110T | 9.7 | 27.8 |
| V111P | 12.0 | 43.2 |
| S119P | 6.2 | 44.0 |
| G127A | 21.0 | 40.0 |
| G207N | 30.5 | 36.3 |

| Variant | AGU/mg |
| --- | --- |
| AMG G2 (wild type) | 1.8 |
| N110T | 3.5 |
| V111P | 3.1 |
| S119P | 2.1 |
| G127A | 5.8 |
| G207N | 5.7 |
| L3N | 2.3 |
| S56A | 2.6 |
| A102* | 2.5 |
| D403S | 2.2 |
| I18V + T51S + S56A + V59T + L60A | 3.3 |
| S119P + Y402F | 2.7 |
| S119P + I189T + Y223F + F227Y + Y402F | 3.0 |

Example 5

Thermostability at 70° C.

An AMG G2 S119P variant was constructed using the approach described in Example 51.

The thermostability was determined as $T_{1/2}$ using Method I, and as % residual activity after incubation for 30 minutes in 50 mM NaOAc, pH 4.5, 70° C., 0.2 AGU/ml, as described in the "Material & Methods" section above. The result of the tests are listed in the Table below and compared to the wild-type *A. niger* AMG G2.

| A. niger AMG (Enzyme) | Residual activity (%) | $T_{1/2}$ (min.) |
|---|---|---|
| S119P variant | 22 | 17 |
| wild-type (SEQ ID NO: 2) | 13 | 8 |

Example 6

Thermostability at 68° C.

AMG G2 variants were constructed using the approach described in Example 3, except for variants nos. 1 and 2 in the Table below, which were prepared by shuffling as described in WO 95/22625 (from Affymax Technologies N.V.). The thermostability was determined as $T_{1/2}$ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ A. niger AMG G2 (wild type) (min) |
|---|---|---|---|
| 1 | A246T + T72I | 11.3 | 8.5 |
| 2 | G447S + S119P | 11.4 | 7.9 |
| 3 | E408R + A425T + S465P + T494A | 8.6 | 8.1 |
| 4 | E408R + S386N | 12.6 | 8.9 |
| 5 | T2P | 9.3 | 8.5 |
| 6 | T2Q + A11P + S394R | 10.7 | 8.5 |
| 7 | T2H | 9.5 | 8.9 |
| 8 | A11E + E408R | 12.7 | 9.3 |
| 9 | T2M + N9A + T390R + D406N + L410R | 10.7 | 8.5 |
| 10 | A393R | 17.7 | 8.4 |
| 11 | T2R + S386R + A393R | 14.1 | 8.4 |
| 12 | A393R + L410R | 14.7 | 7.9 |
| 13 | A1V + L66R + Y402F + N427S + S486G | 11.7 | 8.5 |
| 14 | T2K + S30P + N427M + S444G + V470M | 11.4 | 8.4 |

Thermostability at 70° C. on Purified Samples.

| | Enzyme | T½ (min) |
|---|---|---|
| 15 | AMG G2 (wild type) | 7.4 |
| 16 | T2E + T379A + S386K + A393R | 11.6 |
| 17 | E408R + S386N | 10.2 |
| 18 | T2Q + A11P + S394R | 9.8 |
| 19 | A1V + L66R + Y402F + N427S + S486G | 14.1 |
| 20 | A393R | 14.6 |
| 21 | T2R + S386R + A393R | 14.1 |
| 22 | A393R + L410R | 12.9 |
| 23 | Y402F | 10.1 |

Example 7

Thermostability at 68° C.

AMG G2 variants were constructed by shuffling using the approach described in Example 3 followed by shuffling of positive variants.

The thermostability was determined as T½ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ A. niger AMG G2 (wild type) (min) |
|---|---|---|---|
| 24 | PLASD[i] + V59A + A393R + T490A | 27.2 | 6.8 | i = N-terminal extension

Example 8

Thermostability at 68° C.

AMG G2 variants were constructed using the approach described in Example 3. The thermostability was determined as T½ using method I at 68° C. as described in the "Materials & Methods" section and compared to the wild-type *A. niger* AMG G2 under the same conditions. Evaluation of variants were performed on culture broth after filtration of the supernatants.

| | Variant | T½ (min) | T½ A. niger AMG G2 wild-type (min) |
|---|---|---|---|
| 25 | D357S + T360V + S371H | 6.6 | 5.9 |
| 26 | N313G + F318Y | 8.9 | 5.9 |
| 27 | S356P + S366T | 7.3 | 5.8 |
| 28 | S340G + D357S + T360V + S386P | 7.2 | 5.8 |

Example 9

Thermostability at 70° C.

An AMG G2 variants was constructed using the approach described in Example 1 and evaluated as semi-purified (filtration of culture broth followed by desalting on a G-25 column) samples.

The thermostability was determined as % residual activity using Method I in 50 mM NaOAc, pH 4.5, 70° C., as described in the "Material & Methods" section above. The result of the test is listed in the Table below and compared to the wild-type *A. niger* AMG G2.

| | Enzyme | T½ (min) |
|---|---|---|
| 29 | AMG G2 (wild type) | 7 |
| 30 | Y402F + S411V | 60 |
| 31 | S119P + Y402F + S411V | 115 |
| 32 | S119P + Y312Q + Y402F + T416H | 50 |

Example 10

Thermostability at 70° C. in Presence of 30% Glucose

AMG G2 variants were constructed using the approach described in Example 3.

The thermostability was determined as T/2 using method II at 70° C. as described in the "Materials & Methods" section and compared to the wild-type *A. niger* AMG G2 under the same conditions.

| | Enzyme | T½ (hr) |
|---|---|---|
| 33 | AMG G2 (wild type) | 1.5 |
| 34 | Y402F | 2.5 |
| 35 | A393R | 4.0 |
| 36 | T2R + S386R + A393R | 2.0 |
| 37 | PLASD(N-terminal) + V59A + A393R + T490A | 16.0 |

Example 11

Saccharification Performance of AMG Variants S119P+Y402F+S411V and PLASD(N-Terminal)+V59A+A393R+T490A, Respectively Saccharification performance of the AMG variants S119P+Y402F+S411V and PLASD(N-terminal)+V59A+A393R+T490A, respectively, both having improved thermostability are tested at 70° C. as described below.

Reference enzyme is the wild-type *A. niger* AMG G2. Saccharification is run under the following conditions:

| | |
|---|---|
| Substrate | 10 DE Maltodextrin, approx. 30% DS (w/w) |
| Temperature | 70° C. |
| Initial pH | 4.3 (at 70° C.) |
| Enzyme dosage | 0.24 AGU/g DS |

Saccharification

The substrate for saccharification is made by dissolving maltodextrin (prepared from common corn) in boiling Milli-Q water and adjusting the dry substance to approximately 30% (w/w). pH is adjusted to 4.3. Aliquots of substrate corresponding to 15 g dry solids are transferred to 50 ml blue cap glass flasks and placed in a water bath with stirring. Enzymes are added and pH re-adjusted if necessary. The experiment is run in duplicate. Samples are taken periodically and analysed at HPLC for determination of the carbohydrate composition.

The invention claimed is:

1. An isolated non-naturally occurring variant of a parent *Aspergillus niger* glucoamylase, wherein the variant (a) has at least 95% identity to the amino acid sequence shown in SEQ ID NO: 2; (b) comprises one or more non-naturally occurring substitution(s), insertion(s) and/or deletion(s) in a region between amino acid residues 247-271 of SEQ ID NO:2, except for amino acid substitutions at G251, D257, and/or E259 with A, E, D/Q respectively and (c) catalyzes the release of D-glucose from the non-reducing ends of starch or related oligo- and polysaccharide molecules.

2. The variant of claim 1, wherein the variant has at least 97% identity to the amino acid sequence shown in SEQ ID NO: 2.

3. The variant of claim 1, wherein the variant has at least 99% identity to the amino acid sequence shown in SEQ ID NO: 2.

4. A DNA construct comprising an isolated DNA sequence encoding the glucoamylase variant according to claim 1.

5. A recombinant expression vector which carries a DNA construct according to claim 4.

6. An isolated host cell which is transformed with a DNA construct according to claim 4.

7. The cell of claim 6, which is a microorganism.

8. The cell of claim 6, which is a bacterium or a fungus.

9. The cell of claim 6, which is a protease deficient *Aspergillus oryzae* or *Aspergillus niger*.

10. A process for converting starch or partially hydrolyzed starch into a syrup containing dextrose, said process including the step saccharifying starch hydrolyzate in the presence of a glucoamylase variant of claim 1.

11. The process of claim 10, wherein the dosage of glucoamylase is present in the range from 0.05 to 0.5 AGU per gram of dry solids.

12. The process of claim 10, comprising saccharification of a starch hydrolyzate of at least 30 percent by weight of dry solids.

13. The process of claim 10, wherein the saccharification is conducted in the presence of a debranching enzyme selected from the group of pullulanase and isoamylase.

14. The process of claim 10, wherein the saccharification is conducted at a pH of 3 to 5.5 and at a temperature of 60-80° C. for 24 to 72 hours.

15. A method of saccharifying a liquefied starch solution, which method comprises:

(i) a saccharification wherein one or more enzymatic saccharification stages takes place, and (ii) one or more high temperature membrane separation steps, wherein the enzymatic saccharification is carried out using a glucoamylase variant of claim 1.

16. An isolated variant of a parent glucoamylase, wherein the variant (a) has at least 99% identity to the amino acid sequence shown in SEQ ID NO: 2; (b) comprises one or more substitution(s), insertion(s) and/or deletion(s) in a region between amino acid residues 247-271 of SEQ ID NO:2, except for amino acid substitutions at G251, D257, and/or E259 with A, E, D/Q respectively and (c) catalyzes the release of D-glucose from the non-reducing ends of starch or related oligo- and polysaccharide molecules.

\* \* \* \* \*